United States Patent [19]

Russo

[11] 4,261,363
[45] Apr. 14, 1981

[54] RETENTION CLIPS FOR BODY FLUID DRAINS

[75] Inventor: Ronald D. Russo, Barrington, R.I.

[73] Assignee: C. R. Bard, Inc., Murray Hill, N.J.

[21] Appl. No.: 92,985

[22] Filed: Nov. 9, 1979

[51] Int. Cl.³ .......................................... A61M 27/00
[52] U.S. Cl. ............................ 128/350 R; 128/200.26; 128/DIG. 26
[58] Field of Search ............... 128/350, 347, 348, 349, 128/DIG. 26, 201.14, 200.26

[56] References Cited

U.S. PATENT DOCUMENTS

| | | | |
|---|---|---|---|
| 2,586,940 | 2/1952 | Graham | 128/349 |
| 2,898,917 | 8/1959 | Wallace | 128/350 |
| 3,461,869 | 8/1969 | Harges | 128/348 X |
| 3,487,837 | 1/1970 | Petersen | 128/349 |
| 3,568,679 | 3/1971 | Reif | 128/349 R |
| 3,630,195 | 12/1971 | Santomieri | 128/133 |
| 3,663,965 | 5/1972 | Lee, Jr. et al. | 128/1 R |
| 3,682,180 | 8/1972 | McFarlane | 128/350 R |
| 3,782,383 | 1/1974 | Thompson et al. | 128/214 |
| 3,834,380 | 9/1974 | Boyd | 128/133 |
| 3,863,631 | 2/1975 | Baldwin | 128/214 R |
| 4,069,820 | 1/1978 | Berman | 128/200.26 |
| 4,080,970 | 3/1978 | Miller | 128/350 R |
| 4,129,128 | 12/1978 | McFarlane | 128/133 |

*Primary Examiner*—Stephen C. Pellegrino
*Attorney, Agent, or Firm*—Stephen P. Gilbert

[57] ABSTRACT

A clip for retaining a flexible body fluid drain at a drainage site in a medical patient and preventing movement of the drain is disclosed. The clip has an upper portion containing a longitudinal slot into which the drain may be inserted sideways after placement of the drain in the drainage site, and a base portion, by which the clip may be taped or otherwise secured to the body surface of the patient at the drainage site.

13 Claims, 10 Drawing Figures

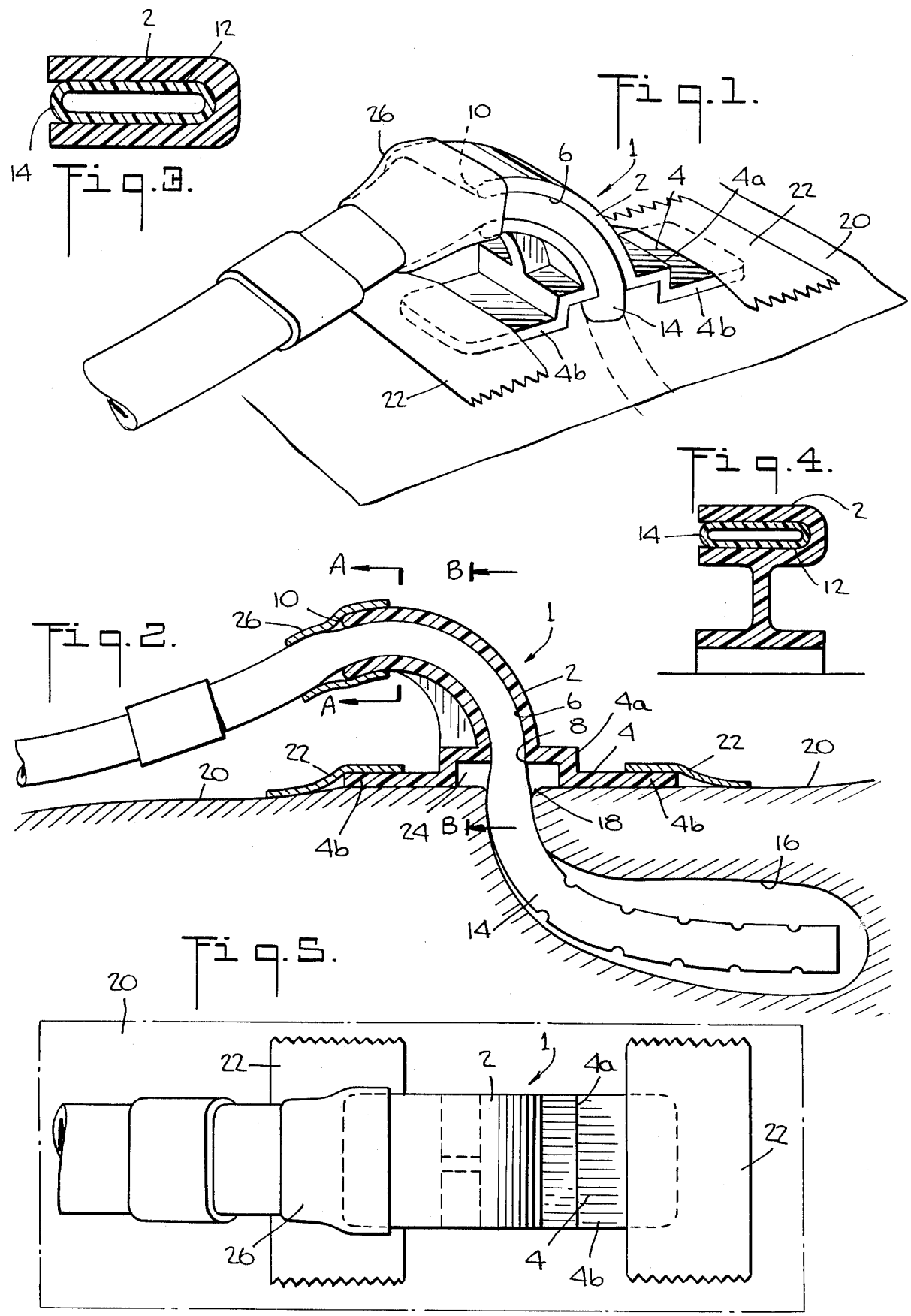

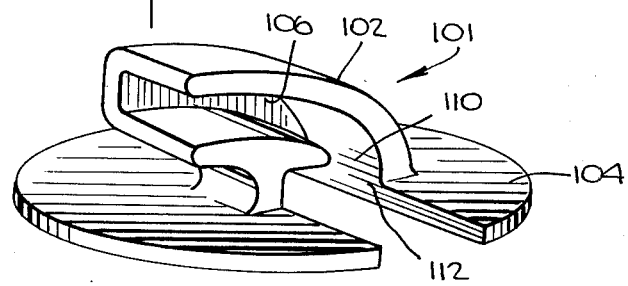
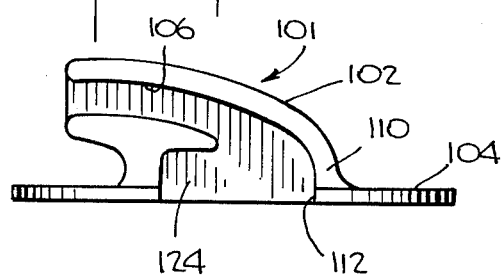
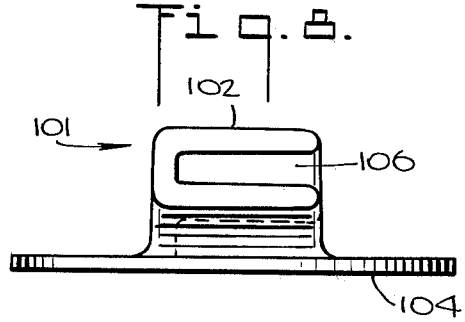
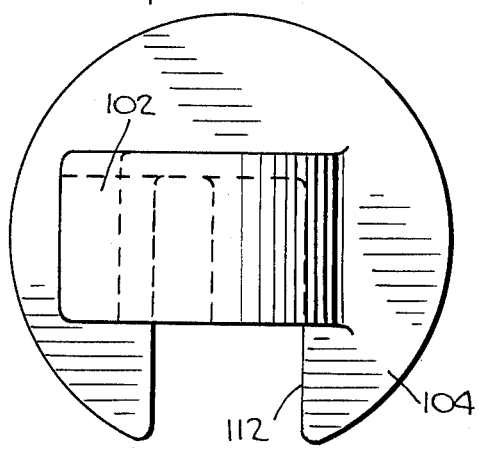
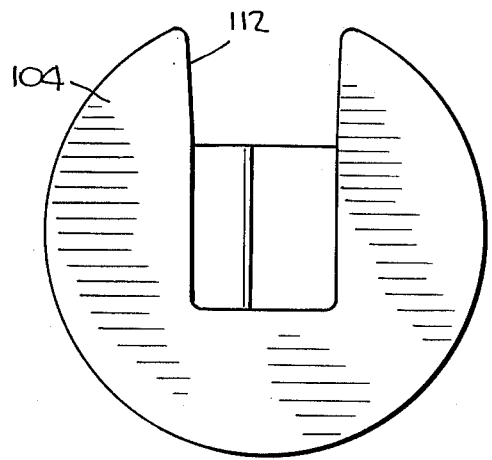

RETENTION CLIPS FOR BODY FLUID DRAINS

BACKGROUND OF THE INVENTION

The placement and retention of a body fluid drain in and on a patient's body is a continuing medical problem. Various devices have been provided to retain and secure a drain as it emerges from a surgically provided or natural body cavity that acts as a drainage site in a patient's body, but many surgeons find these devices unsatisfactory. Hence, various expedients are employed, such as, simply taping the drain to the body surface where it emerges.

Problems with drains include their tendency to pull out of the drainage site because, for example, of movement of the patient. Additionally, drains may become kinked or pinched and, therefore, blocked, due to such movement, particularly if the patient rolls over in bed and lies on the drain. Furthermore, the drain is apt to pop out of the drainage site if suction is employed. These problems inherent in the use of any drainage tube are aggravated by the use of the new silicone-type tubes, which are softer and smoother than more conventional plastic drain tubes.

It is desirable to be able to secure a body fluid drain to the patient so that the drain may first emerge from the body cavity relatively perpendicularly to the body surface, if necessary, and then be curved over into an aspect parallel with the body surface. This minimizes patient discomfort, allows freedom of movement, prevents the drain from being pinched or kinked and blocked, and, at the same time, aids in securely retaining the drain at the drainage site. Because drains may have various cross-sections, for example, round or flat, retention devices should accommodate various shapes. Finally, a retention device should perform its functions efficiently and be foolproof and inexpensive.

Some existing retention devices require threading the drain through the device before placing the drain in the drainage site. However, a doctor should be able to freely place a drain in the drainage site and position it on the body without the initial encumbrance of a retention device on the drain. Also, it is desirable that the retention device used be able to be attached to the drain without threading the drain from an end through the device.

SUMMARY OF THE INVENTION

A retention clip satisfying these requirements has now been developed. The retention clip has an upper portion that contains a longitudinal retention slot which allows a drain that has been placed in the body to be inserted sideways into the clip. The top and bottom walls of the slot may be flat, although not necessarily parallel. Preferably, at least the outer end of the upper portion and its retention slot are substantially parallel to the base portion, and, preferably, the upper portion and its slot are arcuately formed. This prevents crimping of the drain, which may be exiting the body perpendicularly, and allows the drain to lie against and be taped to the body surface close to the point at which the drain emerges from the body.

The upper portion at its inner end is attached to a body-abutting base portion, which is preferably flexible and resilient so as to conform readily to the body surface at the drainage site. The clip may be secured in place by placing adhesive tape over the base portion and onto the adjacent body surface. In some cases it may be desirable to secure the base by sutures through it into the body tissue. The clip may be made inexpensively as an integrally molded item (for example, by injection molding) of a semi-resilient material, such as, polyvinyl chloride (PVC).

BRIEF DESCRIPTION OF THE DRAWINGS

In order to illustrate various embodiments of the invention, the following drawings are provided in which:

FIG. 1 is a perspective view, showing one form of the retention clip into which a flat drain has been inserted and secured after placement in a drainage site;

FIG. 2 is a side view of the clip of FIG. 1;

FIG. 3 is a cross-sectional view taken along line A—A in FIG. 2;

FIG. 4 is a cross-sectional view taken along line B—B in FIG. 2;

FIG. 5 is a top view of the clip and drain shown in FIG. 1;

FIG. 6 is a perspective view of the preferred device of the present invention;

FIG. 7 is a side view of the clip of FIG. 6;

FIG. 8 shows an end view of the retention clip of FIG. 6 from the left side of FIG. 7;

FIG. 9 is a top view of the device of FIG. 6; and

FIG. 10 is a bottom view of the device of FIG. 6.

DETAILED DESCRIPTION OF THE INVENTION

The upper portion of the new retention clip should be rigid enough so that if the patient lies on the clip, the drain is not kinked or crushed. The base of the clip should be deformable enough so that it will readily conform to the patient's body, and if the clip is to be sutured to the patient, the base should be sufficiently penetrable. If the clip is to be adhesively secured (e.g., taped) to the patient, the base of the clip preferably should be thin. The two portions of the clip (upper and base) may be made separately and of different materials and then joined, or the clip may be made of a single material at one time, as by injection molding. The material, preferably, should have sufficient tack to aid in holding the drain within the slot. A semi-resilient material, for example, polyvinyl chloride, is preferred.

One form of the retention clip is shown at 1 in FIGS. 1 through 5. The clip includes upper drain retention portion 2 and body-abutting base portion 4. Upper portion 2 has slot 6 extending longitudinally from inner end 8 of upper portion 2 to outer end 10 of upper portion 2. Interior 12 of slot 6 is arranged to receive and hold flat drain 14. (The internal cross-section of the upper portion of the clip may be varied to accommodate round drains or drains of other cross-sections.) Usually, the drain is first positioned in body cavity 16 at drainage site 18 and then inserted sideways into slot 6; however, the clip may be placed on the drain before the drain is positioned in the body.

Base 4 is secured to body surface 20 of the patient at drainage site 18 by adhesive tape 22, and the clip will retain drain 14 substantially in the desired, predetermined position. Alternatively, sutures may be used instead of tape because they are more secure.

The end of slot 6 at inner end 8 of upper portion 2 has an enlargement forming recess 24 in base 4 to prevent pinching and inadvertent closure of drain 14. Such pinching might occur because of sideways movement of the clip caused, for example, by the patient rolling on it or moving about. Base 4 has upper part 4a, which provides the enlargement and recess 24, and lower flat portions 4b, which lie on body surface 20.

As best seen in FIG. 1, upper portion 2, including slot 6, extends arcuately away from base 4, and the segment of upper portion 2 nearest outer end 10 is substantially parallel to base flange 4 so that drain 14 exits the clip substantially parallel and close to body surface 20. Thus, the clip turns drain 14 from a direction extending substantially perpendicular to outer surface 20 to a direction substantially parallel to outer surface 20. This allows the drain to be secured to the body close to where it exits the body to prevent movement of the drain and provide for patient comfort.

The inner surface of slot 6 is proportioned to fit snugly against drain 14 so as to retain drain 14 firmly in a relatively longitudinal direction after the clip is slid onto the drain. Internal ribs (not shown) along the inner surface of slot 6 may also be provided to aid in holding the drain firmly. Additional tape 26 or a metal clip or sutures may also be used to secure the drain to the clip. (Sutures have the advantage of allowing the surgeon to adjust the compression on the drain because of the resiliency of the clip.) As noted above, if the upper portion is of a material having sufficient tack, this will aid in retaining the drain within the clip. PVC is such a material.

FIGS. 6 to 10 show preferred retention clip 101, essentially in proportion. It comprises upper portion 102 and body abutting base portion 104 having internal arcuately formed slot 106. Base 104 substantially surrounds inner end 110 of upper portion 102 and has inwardly extending opening 112 extending to slot 106 to allow a drain (not shown) to be inserted sideways through opening 112 and into slot 106. Recess 124 prevents the drain from being pinched at the drainage site. A typical clip 101 has a base 104 diameter of 1.5 inches.

Variations in and modifications to the invention will be apparent to one skilled in the art. The claims are intended to cover all such modifications and variations as fall within the true spirit and scope of the invention.

I claim:

1. A retention clip for a flexible body fluid drain, a portion of which drain is positioned in a body cavity, the drain exiting the body at a drainage site, said clip comprising:
    (a) an upper portion having an inner end and an outer end and having a slot extending longitudinally from the outer end to the inner end, wherein a side of the upper portion is open to permit the drain to be inserted sideways into the slot; and
    (b) a body-abutting base portion attached to the inner end of the upper portion, the inner end of the upper portion having an enlargement forming a recess at the base portion to prevent pinching of the drain by the clip at the drainage site and the base portion having an opening communicating with the slot to allow the drain to be inserted sideways into the slot.

2. A retention clip according to claim 1 wherein the base portion is relatively thin and flat and thereby adapted to be adhesively taped to the body to secure the clip and the drain at the drainage site.

3. A retention clip according to claim 1 wherein the base portion is sufficiently penetrable so that it can be sutured to the body to secure the clip and the drain at the drainage site.

4. A retention clip according to claim 1 wherein the portion of the slot nearest the outer end of the upper portion extends substantially parallel to the base portion so as to lead the drain into a position extending substantially parallel and close to the surface of the body.

5. A retention clip according to claim 1 wherein the upper portion and base are formed as an integral piece.

6. A retention clip according to claim 5 formed of a semi-resilient material.

7. A retention clip according to claim 1 formed of polyvinyl chloride.

8. A retention clip according to claim 1 in which the upper portion and its slot extend arcuately away from the base portion to lead the drain into a position extending substantially parallel and close to the surface of the body.

9. A retention clip according to claim 1 in which the cross-section of the slot is substantially rectangular to retain a flat drain.

10. A retention clip for a flexible body fluid drain, a portion of which drain is positioned in a body cavity, the drain exiting the body at a drainage site, said clip comprising:
    (a) an upper portion having an inner end and an outer end and having a slot extending longitudinally from the outer end to the inner end, wherein a side of the upper portion is open to permit the drain to be inserted sideways into the slot; and
    (b) a relatively thin body-abutting base portion attached to the inner end of the upper portion and having an inwardly extending opening communicating with the slot to allow the drain to be inserted sideways into the slot;

wherein the inner end of the upper portion has an enlargement forming a recess at the base portion to prevent pinching of the drain by the clip at the drainage site and the portion of the slot nearest the outer end of the upper portion extends substantially parallel to the base portion so that the drain is led into a position extending substantially parallel and close to the surface of the body.

11. A retention clip according to claim 10 formed as an integral piece of a semi-resilient material.

12. A retention clip according to claim 11 formed of polyvinyl chloride.

13. The retention clip of claim 10 wherein the upper portion is arcuately formed.

* * * * *